(12) United States Patent
Ura et al.

(10) Patent No.: US 11,199,515 B2
(45) Date of Patent: Dec. 14, 2021

(54) GAS SENSOR DEVICE INCLUDING COIL-SHAPED HEATER, SUSPENDED DETECTOR AND CAP WITH THROUGH HOLE AND METHOD OF MANUFACTURING SAME

(71) Applicant: Nissha Co., Ltd., Kyoto (JP)

(72) Inventors: Yuki Ura, Itami (JP); Muneharu Shimabukuro, Itami (JP); Shinichi Matsumoto, Itami (JP)

(73) Assignee: NISSHA CO., LTD., Kyoto (JP)

( * ) Notice: Subject to any disclaimer, the term of this patent is extended or adjusted under 35 U.S.C. 154(b) by 458 days.

(21) Appl. No.: 16/160,164

(22) Filed: Oct. 15, 2018

(65) Prior Publication Data
US 2019/0064093 A1    Feb. 28, 2019

Related U.S. Application Data

(63) Continuation of application No. PCT/JP2017/016655, filed on Apr. 27, 2017.

(30) Foreign Application Priority Data

May 9, 2016    (JP) .............................. JP2016-093837

(51) Int. Cl.
*G01N 27/12*    (2006.01)
*G01N 33/00*    (2006.01)
*G01N 27/00*    (2006.01)

(52) U.S. Cl.
CPC ......... *G01N 27/12* (2013.01); *G01N 33/0009* (2013.01); *G01N 27/00* (2013.01)

(58) Field of Classification Search
CPC .... G01N 27/12; G01N 27/00; G01N 33/0009; G01N 27/122; G01N 33/004; G01N 27/18; G01N 33/0047
See application file for complete search history.

(56) References Cited

U.S. PATENT DOCUMENTS 6,058,020 A * 5/2000 Winterer ................. H01L 23/13
                                                    361/767
2001/0003916 A1   6/2001 Nomura et al.
2002/0092341 A1*  7/2002 Cardinale ............... G01N 27/12
                                                    73/25.01

FOREIGN PATENT DOCUMENTS

| JP | H07-198644 A | 8/1995 |
| JP | 2001-174426 A | 6/2001 |
| JP | 2011-237220 A | 11/2011 |

OTHER PUBLICATIONS

International Search Report dated Jul. 25, 2017 for corresponding foreign Application No. PCT/JP2017/016655, 2 pp.

* cited by examiner

*Primary Examiner* — Eric S. McCall
*Assistant Examiner* — Timothy P Graves
(74) *Attorney, Agent, or Firm* — United IP Counselors, LLC

(57) ABSTRACT

A gas sensor device includes a package including a cap in which a through hole for taking gas is formed and a base in which a recessed portion is formed. The cap is attached to the base so that a space is defined around the recessed portion. The device includes metal electrodes fixed to portions surrounding the recessed portion and embedded in the base. The device includes a gas detecting element, which includes a gas detector having a coil-shaped heater that is heated when detecting a predetermined gas, and a plurality of metal lead wires extending from the gas detector to the electrodes. The gas detecting element is held in a suspended state in the recessed portion and/or a space above the recessed portion with the plurality of lead wires, so that the gas detecting element, which includes the heater, does not make contact with walls of the recessed portion.

20 Claims, 15 Drawing Sheets

GAS SENSOR DEVICE INCLUDING COIL-SHAPED HEATER, SUSPENDED DETECTOR AND CAP WITH THROUGH HOLE AND METHOD OF MANUFACTURING SAME

CROSS-REFERENCE TO RELATED APPLICATIONS

This application is a continuation application of PCT Application No. PCT/JP2017/016655 filed on Apr. 27, 2017. The entire disclosure of PCT Application No. PCT/JP2017/016655 is hereby incorporated herein by reference.

This application claims priority under 35 U.S.C. § 119 to Japanese Patent Application No. 2016-093837 filed on May 9, 2016. The entire disclosure of Japanese Patent Application No. 2016-093837 is hereby incorporated herein by reference.

BACKGROUND

Technical Field

The present disclosure relates to a gas sensor device for detecting a specific gas and a method of manufacturing the same.

Background Information

Among gas sensor devices using a gas detecting element for detecting a specific gas, there is one in which the gas detecting element includes a gas detector having a coil-shaped heater so as to heat the gas detector that responds to the gas to be detected. For example, Patent Citation 1 (JP-A-H7-198644) discloses a gas sensor device in which a coil-shaped heater is embedded in a gas-sensitive metal oxide semiconductor to form a gas detector. This coil-shaped heater also functions as an electrode for taking a signal from the gas detector.

When heating the gas detecting element for detecting a specific gas, the coil-shaped heater is supplied with electricity for heating, and hence power consumption is apt to increase. If the gas sensor device is being incorporated in an apparatus such as a mobile phone that works with a battery while the power consumption of this heater is large, in case where, it is assumed that working time of the apparatus's original function is shortened. Such a gas sensor device has a problem that use of the gas sensor device is limited more as the power consumption becomes larger.

Power consumption of the gas sensor device can be suppressed by downsizing the gas detecting element, for example. However, unless a package of the gas sensor device housing the downsized gas detecting element is balanced with the size of the gas detecting element, the problem that it is difficult to incorporate it in a relatively small apparatus such as a mobile phone is still unsolved.

BRIEF SUMMARY

It is an object of the present disclosure to provide a compact gas sensor device equipped with a gas detector including a coil-shaped heater having reduced power consumption.

These and other objects, features, aspects and advantages of the present disclosure will become apparent to those skilled in the art from the following detailed description, which, taken in conjunction with the annexed drawings, discloses a preferred embodiment of the present advancement.

Aspects of the present disclosure are explained below as the technical solution. These aspects can be arbitrarily combined as needed.

A gas sensor device according to one aspect of the present disclosure comprises:

a package including a cap in which a through hole for taking gas is formed and a base in which a recessed portion is formed, a height of the package being 5 mm or less from an uppermost portion of the cap to a lowermost portion of the base, in a state where the cap is attached to the base so that a space is defined around the recessed portion;

a plurality of metal electrodes fixed to portions surrounding the recessed portion and embedded in the base; and a gas detecting element, which includes a gas detector having a coil-shaped heater that is heated when detecting a predetermined gas, and a plurality of metal lead wires extending from the gas detector to the plurality of electrodes.

The gas detecting element is held in a suspended state in the recessed portion and/or a space above the recessed portion with the plurality of lead wires, so that the gas detector, which includes the heater, does not make contact with walls of the recessed portion.

In the above-described gas sensor device according to one aspect of the present disclosure, the plurality of metal lead wires are connected to the metal electrodes disposed surrounding the recessed portion of the base, and hence the gas detector, including the heater, is held in a suspended state in the recessed portion and the space above the recessed portion. Therefore, as the gas detector is made smaller, the recessed portion is made smaller, and the electrodes, which are accurately disposed to surround the recessed portion, are also made smaller and disposed more densely. As a result, an occupied area of the recessed portion and the electrodes can be reduced, and hence the entire shape of the gas sensor device can be downsized.

In the above-described gas sensor device, the cap can have a plurality of the through holes formed in parts other than a part just above the gas detector. This structure prevents dust and water from adhering to the gas detector.

In the above-described gas sensor device, each of the plurality of electrodes can have a first crank and a second crank bent in opposite directions in an upper part and in a lower part, and a part between the first crank and the second crank that is embedded in the base. Each of the electrodes has a side closer to one end than the first crank that is exposed upward from the base, and a side closer to the other end than the second crank that is exposed downward from the base.

According to the above-described structure, since the exposed upper part region from the first crank to the one end spreads in a two-dimensional manner, the lead wires can be easily placed. In addition, since the exposed lower part region from the second crank to the other end spreads in a two-dimensional manner, easy contact shape as a device terminal can be achieved. Since the part between the first crank and the second crank is embedded, the electrodes are securely fixed, and the gas detecting element can also be securely fixed to the package.

In the above-described gas sensor device, at least one of the plurality of lead wires can form the heater in which a part of lead wire is coiled in five or less turns in the gas detecting element. Since the number of turns of the coil-shape heater is five or less, the heater can be easily downsized, and hence the gas detecting element can be small, so that downsizing of the gas sensor device can be achieved.

In the above-described gas sensor device, the plurality of lead wires can include a first lead wire extending from the gas detector, and second and third lead wires extending directly from the coil-shaped heater. The plurality of electrodes can include a first electrode, a second electrode, and a third electrode. The second lead wire can be welded to the second electrode. The third lead wire can be welded to the third electrode. The first electrode can be disposed at a frontmost position. A distance from a rear end of the first electrode to a front end of the second electrode can be longer than a distance from the rear end of the first electrode to a front end of the third electrode.

According to the above-described structure, the second lead wire and the third lead wire, which extend directly from the coiled heater, are offset from each other due to the shape of the heater. However, although the second lead wire and the third lead wire are offset due to the shape of the heater, since the second electrode and the third electrode are disposed at appropriate positions for the second lead wire and the third lead wire, the gas sensor device can be easily downsized.

A method of manufacturing a gas sensor device according to one aspect of the present disclosure comprises:

preparing a cap in which a through hole for taking gas is formed;

forming a base in which a plurality of metal electrodes are embedded, the base having a recessed portion surrounded by the plurality of electrodes and a height of 5 mm or less;

electrically welding the lead wires to the electrodes by placing a plurality of metal lead wires, which extend from a gas detector including a heater, on the plurality of electrodes, and by bringing power supply lines of a welding machine to contact with the lead wire and the electrode from above and below of the base in vertical and horizontal ranges of the base, so that the gas detector is suspended in the recessed portion and/or a space above the recessed portion, without contacting with walls of the recessed portion; and attaching the cap to the base so as to assemble a package having a length, a width, and a height of 5 mm or less each.

In the method of manufacturing the gas sensor device according to one aspect of the present disclosure, the electric welding is performed in the state where the plurality of metal lead wires, which extend from the coil-shaped heater, are placed on the plurality of electrodes embedded in the base, and the gas detector is suspended in the recessed portion and the space above the recessed portion so that the gas detector does not contact with walls of the recessed portion. Furthermore, the power supply lines of the welding machine contact with the lead wires and the electrode respectively from above and below the base within the vertical and horizontal ranges of the base. In the above-described state, the lead wire is electrically welded to the electrode, so that the electrode can be within a vertical range of 5 mm and a horizontal range of 5 mm. In addition, because the two power supply lines of a welding machine are made contact from above and below, they can contact more easily than a case where the both power supply lines are made contact from above, thereby making it easier to manufacture the gas sensor device.

According to the above-described method of manufacturing the gas sensor device, in the base forming step, openings communicating a bottom part and the plurality of electrodes can be formed by fixing pins for holding the electrodes. In the electrically welding step, the power supply line can be brought to contact with the electrode through the openings.

According to the manufacturing method configured as described, since the openings are formed by the fixing pins simultaneously when the base is formed, the openings can be formed without increasing the number of manufacturing steps. Further, by inserting the power supply line in each of the openings, the power supply lines can be easily positioned contacting with the electrodes, and hence electric welding can be performed fast and easily, so that manufacturing time can be reduced.

According to the gas sensor device and the method of manufacturing the same of the present disclosure, it is possible to provide a compact gas sensor device equipped with a gas detector including a coil-shaped heater having reduced power consumption compared to the past.

BRIEF DESCRIPTION OF THE DRAWINGS

Referring now to the attached drawings which form a part of this original disclosure.

DETAILED DESCRIPTION OF THE EMBODIMENTS

Selected embodiments of the present advancement will now be explained with reference to the drawings. It will be apparent to those skilled in the art from this disclosure that the following descriptions of the embodiments of the present disclosure are provided as examples only and are not meant to limit the advancement defined by the appended claims and their equivalents.

(1) Size of Gas Sensor Device

Figure 1:
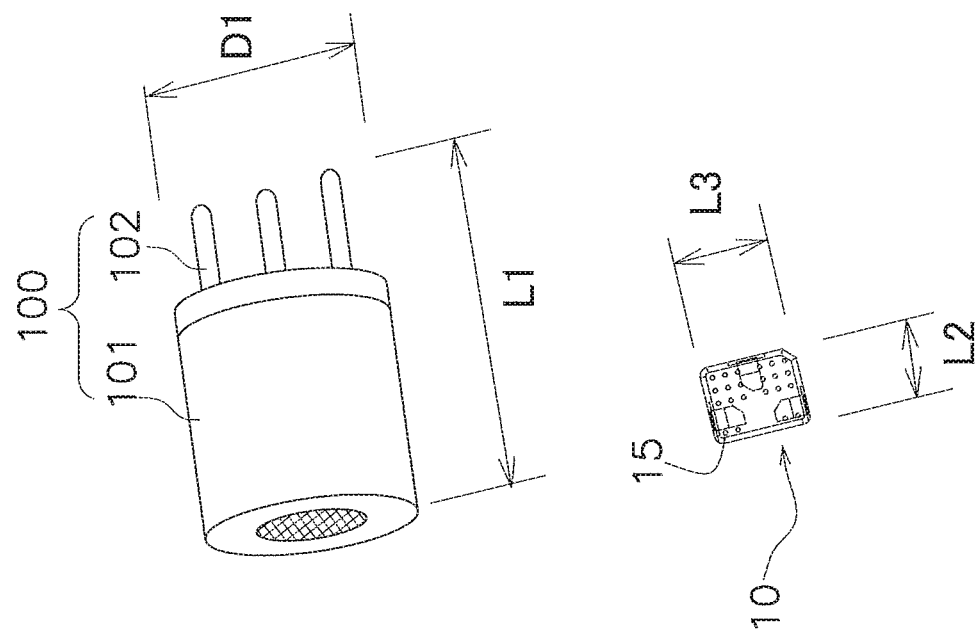
FIG. 1 is a perspective view for comparing a size of a gas sensor device of an embodiment with a size of a conventional gas sensor device.
Figure 1:
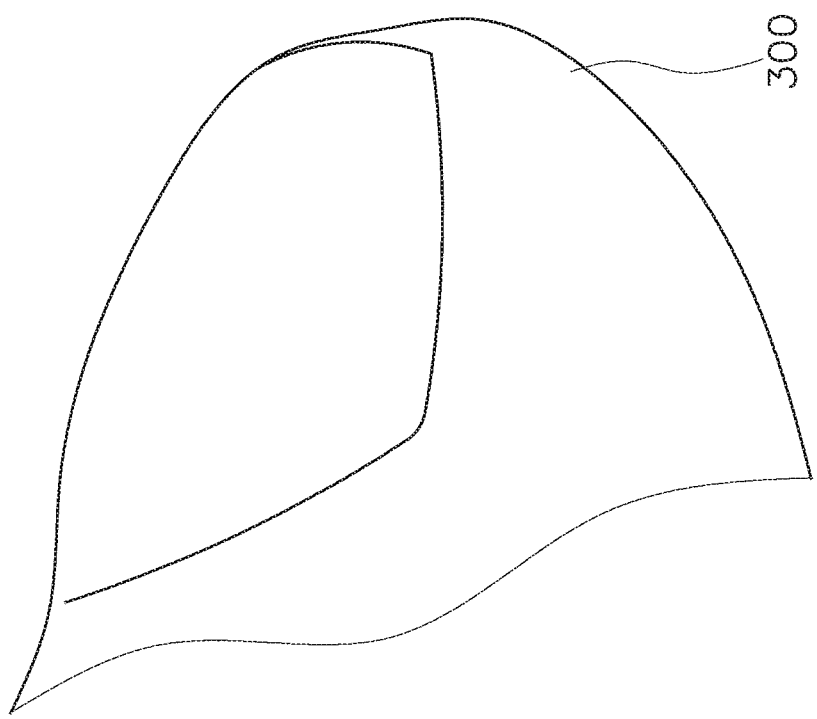

FIG. 1 shows a gas sensor device according to one embodiment of the present disclosure and a conventional gas sensor device. More specifically, FIG. 1 shows a gas sensor device 10 according to the embodiment, a conventional gas sensor device 100, and a thumb 300 placed on a horizontal table for comparison based on a photograph of them.

A size of the conventional gas sensor device 100 is approximately 7.5 mm at a diameter D1 of a cylindrical package 101, for example. The conventional gas sensor device 100 has three terminals 102 protruding from the cylindrical package 101, and a length L1 from a top surface of the package 101 to the end of the terminal 102 is approximately 13 mm, for example.

It is understood that the gas sensor device 10 according to the embodiment is very small compared with the conventional gas sensor device 100 as well as a human thumb 300. The external shape of the gas sensor device 10 is substantially a rectangular solid. A vertical length L2 of a package 15 of the illustrated gas sensor device 10 is approximately 2.7 mm, and a horizontal length L3 is approximately 3.4 mm. In addition, a height H1 of the package 15 of the gas sensor device 10 is approximately 1.25 mm (see FIG. 20).

(2) Outline of Structure of Gas Sensor Device

Figure 2:
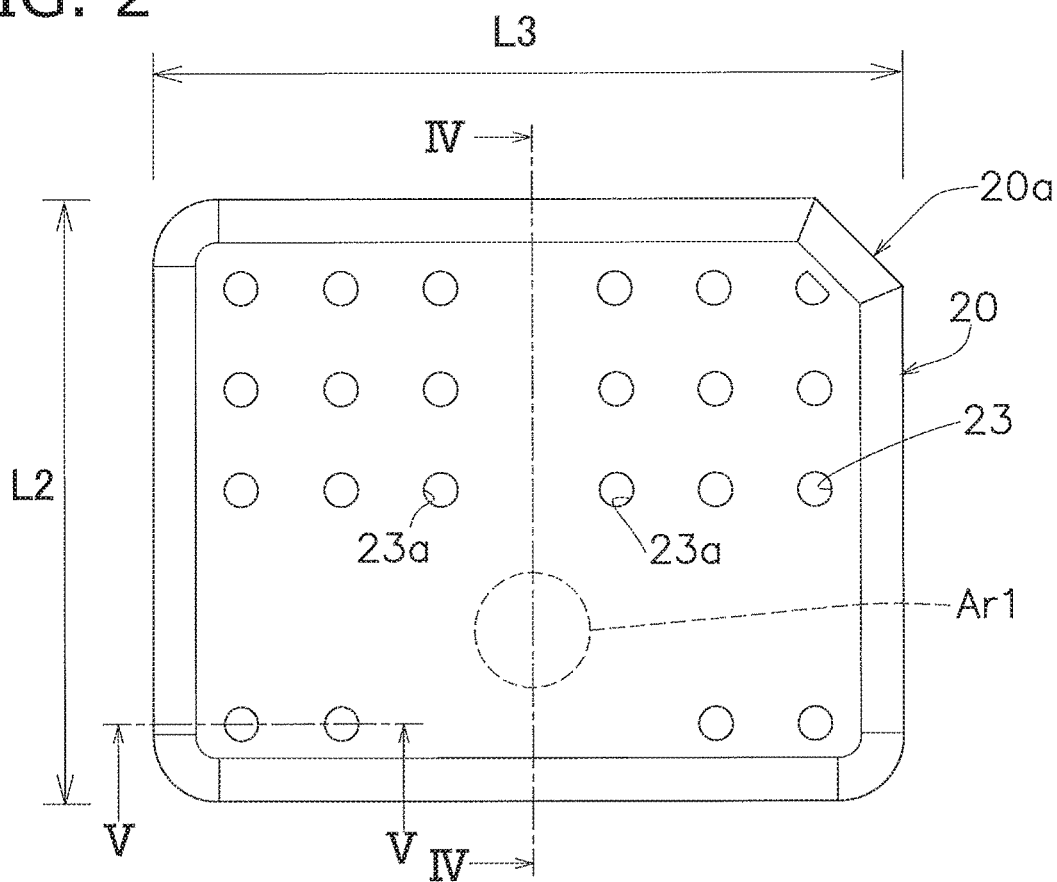
FIG. 2 is a plan view showing a cap of the gas sensor device.
Figure 3:
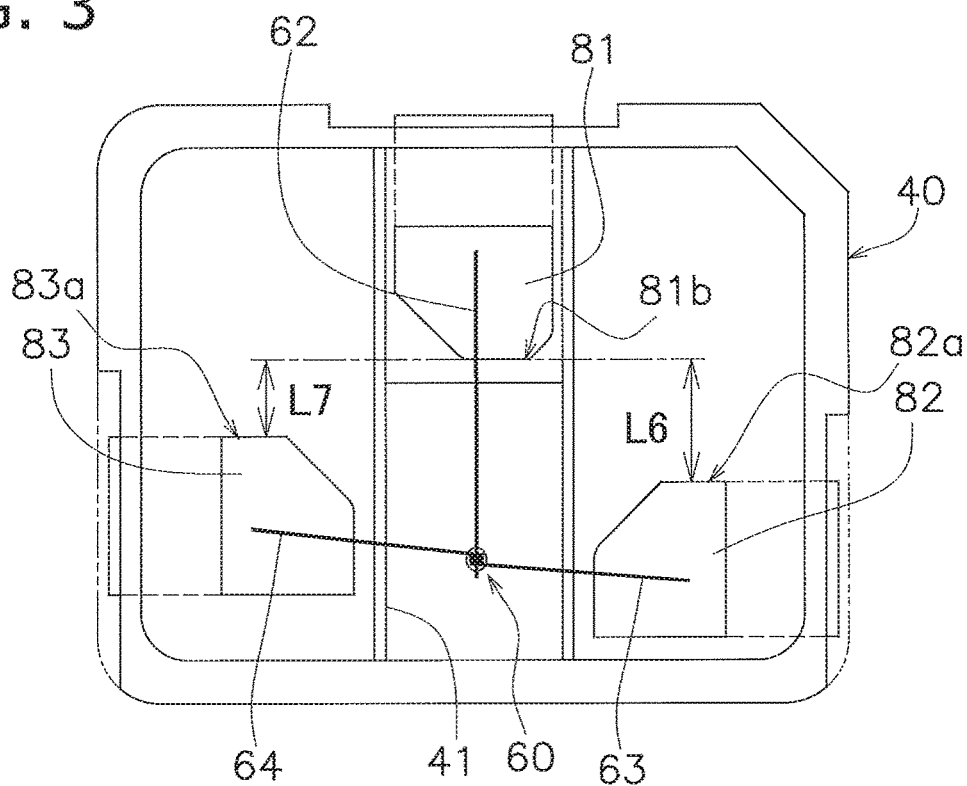
FIG. 3 is a plan view showing a base to which a gas detecting element is attached.

The gas sensor device 10 includes a cap 20 shown in FIG. 2 as well as a base 40 and a gas detecting element 60 shown in FIG. 3. The base 40 is engaged with the cap 20. The gas detecting element 60 is housed in a space surrounded by the cap 20 and the base 40.

(2-1) Gas Detecting Element

Figure 4:
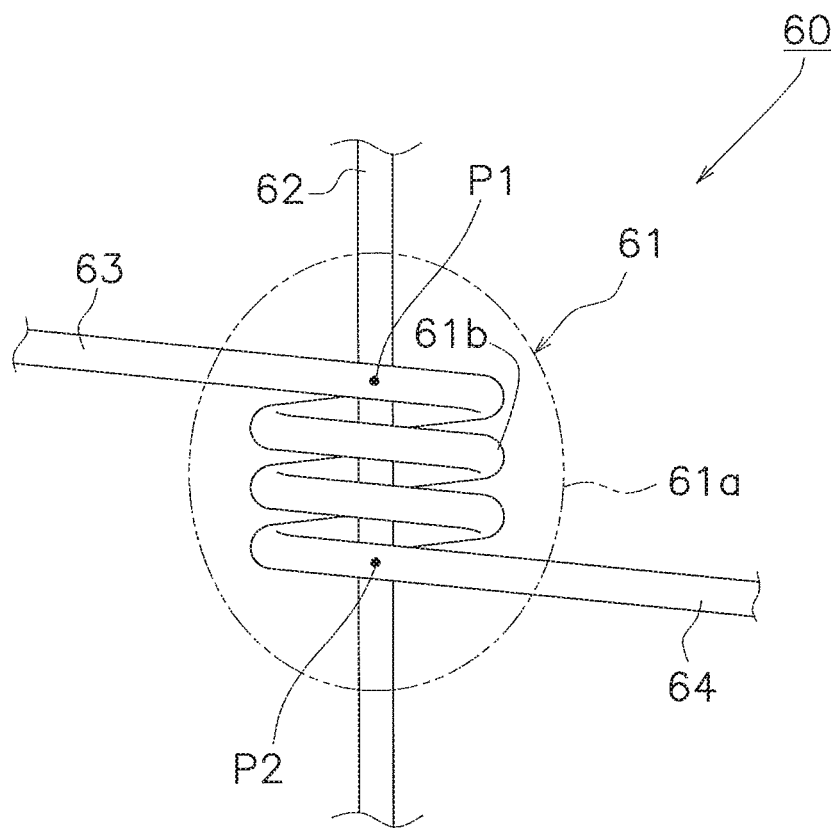
FIG. 4 is an enlarged partial plan view in which a part of the gas detecting element is enlarged.

As shown in FIG. 4, the gas detecting element 60 includes a gas detector 61 for detecting a specific gas. From the gas detector 61, three wires, i.e. a first lead wire 62, a second lead wire 63, and a third lead wire 64 extend outward so as to output electrical phenomenon generated in the gas detector 61. The first to third lead wires 62 to 64 can be platinum wires having a diameter of 15 μm, for example. The diameter of the first to third lead wires 62 to 64 is preferably 15 μm or less in order to obtain appropriate resistance of a coil-shaped heater 61b by a small number of turns. The first lead wire 62 extends in two directions from the gas detector 61, and one extending part out of two directions is an incidental part as a by-product, which is not connected to anywhere and does not work as a lead wire. Therefore the first lead wire 62 is counted as one although it extends in two directions from the gas detector 61.

The shape of the gas detector 61 is, for example, a sphere, a rugby ball shape, or a spheroid. In other words, the gas detector 61 has a bead shape. The gas detector 61 includes a coil-shaped heater 61b inside and has a structure in which a gas sensing body 61a made of metal oxide semiconductor wraps around the coil-shaped heater 61b. This gas sensing body 61a can be formed of a metallic oxide selected from a group consisting of tin oxide, tungstic oxide, indium oxide, zinc oxide, titanium oxide, strontium titanate, barium titanate, and barium stannate, for example. The gas detector 61 can be formed by baking powder of the metallic oxide, for example. Volume of the gas detector 61 is, for example, 0.0001 mm$^3$ or more to 0.01 mm$^3$ or less, preferably 0.0001 mm$^3$ or more to 0.003 mm$^3$ or less, and more preferably 0.0001 mm$^3$ or more to 0.002 mm$^3$ or less. For example, when using the coil-shaped heater 61b that is made of platinum wire having a diameter of 15 μm and has an outer diameter of 110 μm and a length in a central axis direction of 130 μm, the gas detector 61 having a volume of 0.0008 mm$^3$ can be obtained, for example.

The coil-shaped heater 61b existing inside the gas detector 61 is formed by winding a middle part of one platinum wire in a coil shape. Further two platinum wires extending from the coil-shaped heater 61b become the second lead wire 63 and the third lead wire 64. The number of turns of the coil-shaped heater 61b shown in FIG. 4 is substantially three. In this description, the number of turns of the heater 61b is counted, viewed from the longitudinal direction of the coil, between a point P1 at which the second lead wire 63 begins to turn and a point P2 at which the third lead wire 64 begins to turn, as the number of wire elements overlapping with one of the points, e.g. the point P1. In order to downsize the gas detecting element 60, the number of turns is preferably five or less.

(2-2) Base

Figure 5:
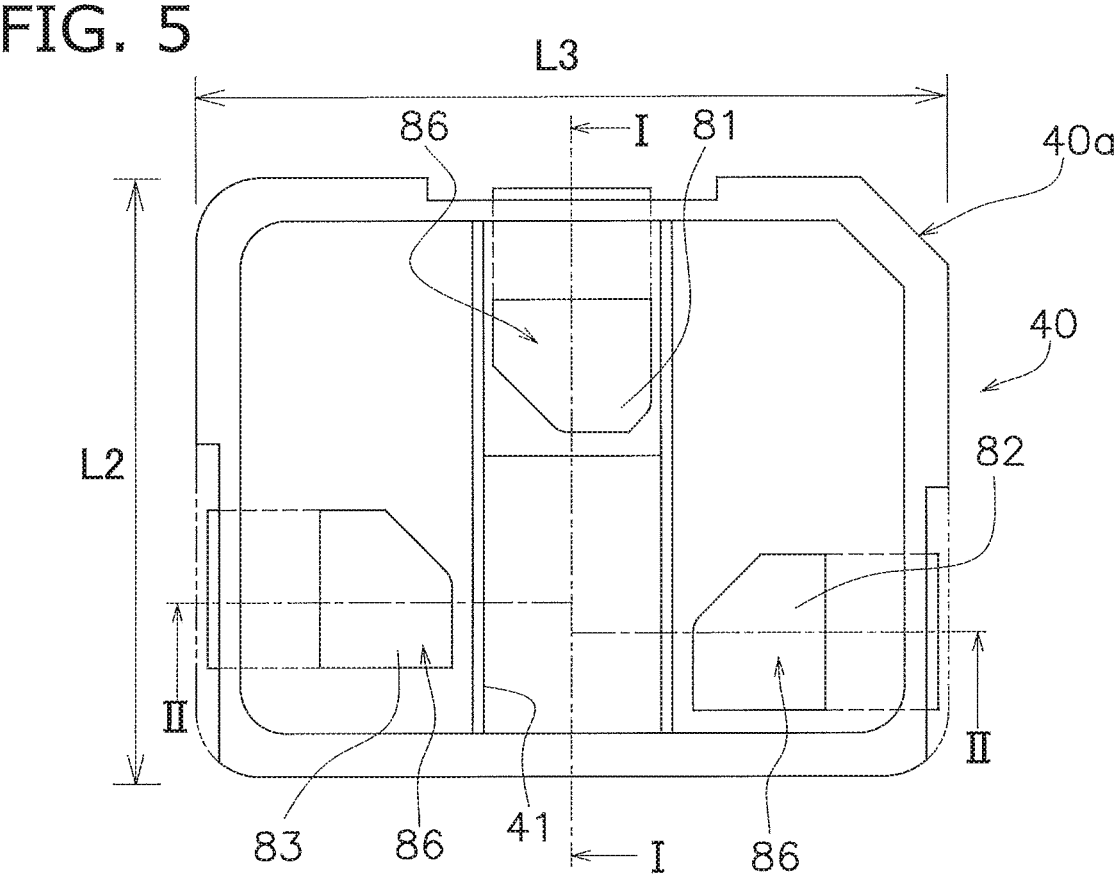
FIG. 5 is a plan view showing a base of the gas sensor device.
Figure 6:
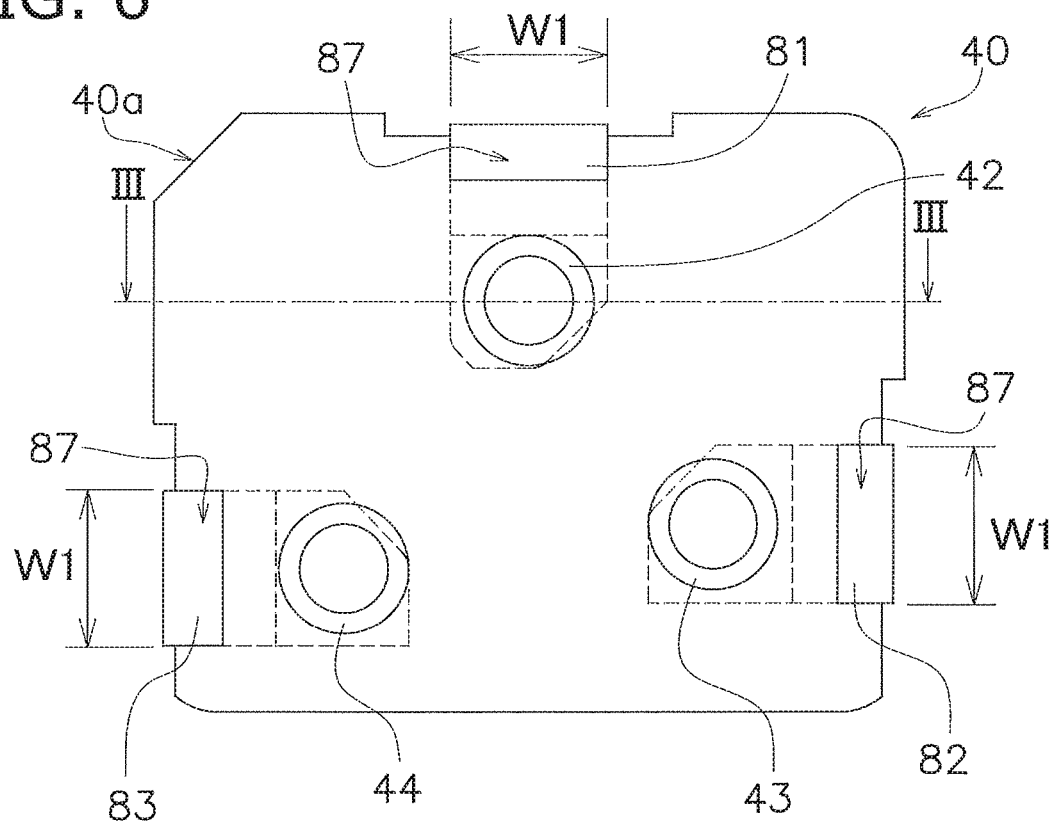
FIG. 6 is a bottom view of the base.
Figure 7:
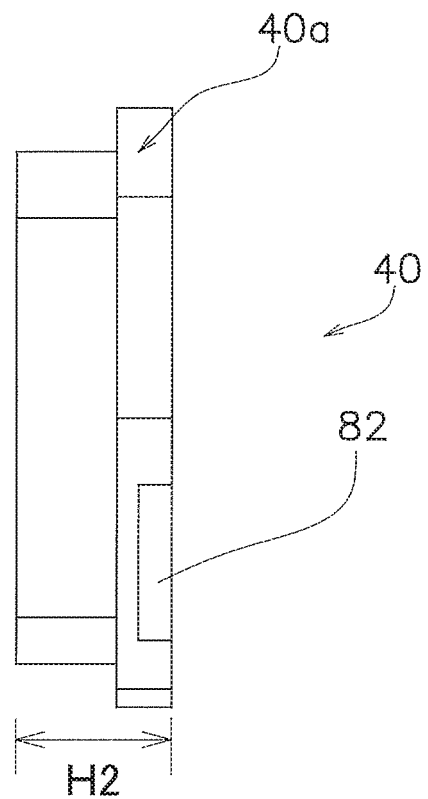
FIG. 7 is a right side view of the base.
Figure 8:
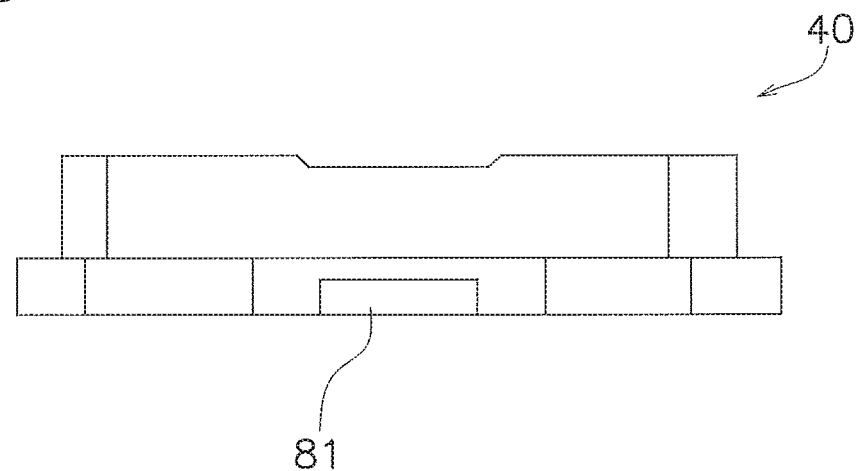
FIG. 8 is a front view of the base.
Figure 9:
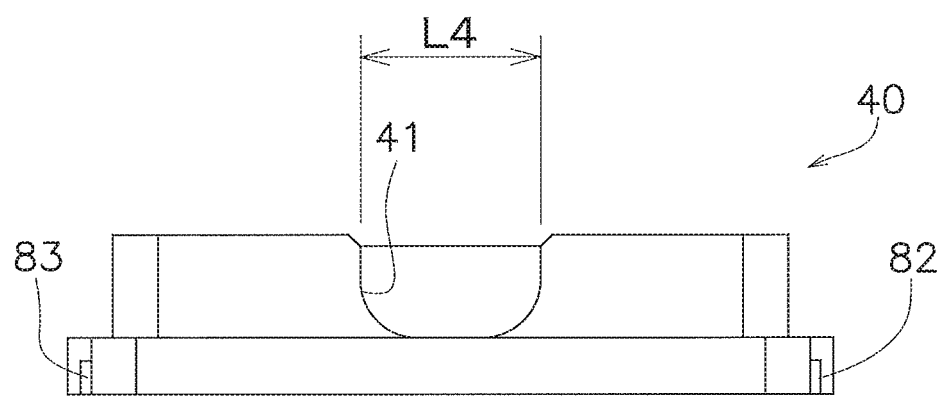
FIG. 9 is a rear view of the base.
Figure 10:
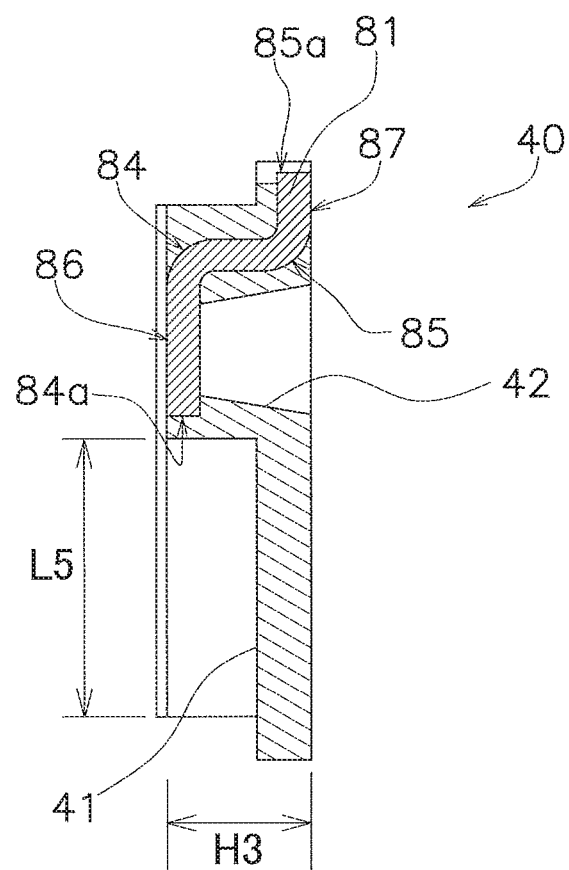
FIG. 10 is a cross-sectional view of the base taken along I-I line in FIG. 5.
Figure 11:
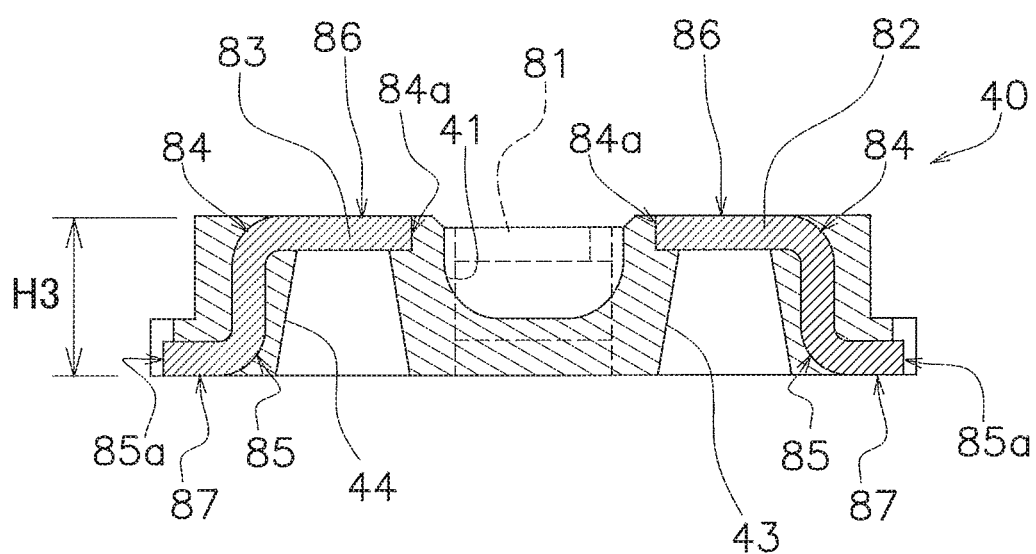
FIG. 11 is a cross-sectional view of the base taken along II-II line in FIG. 5.
Figure 12:
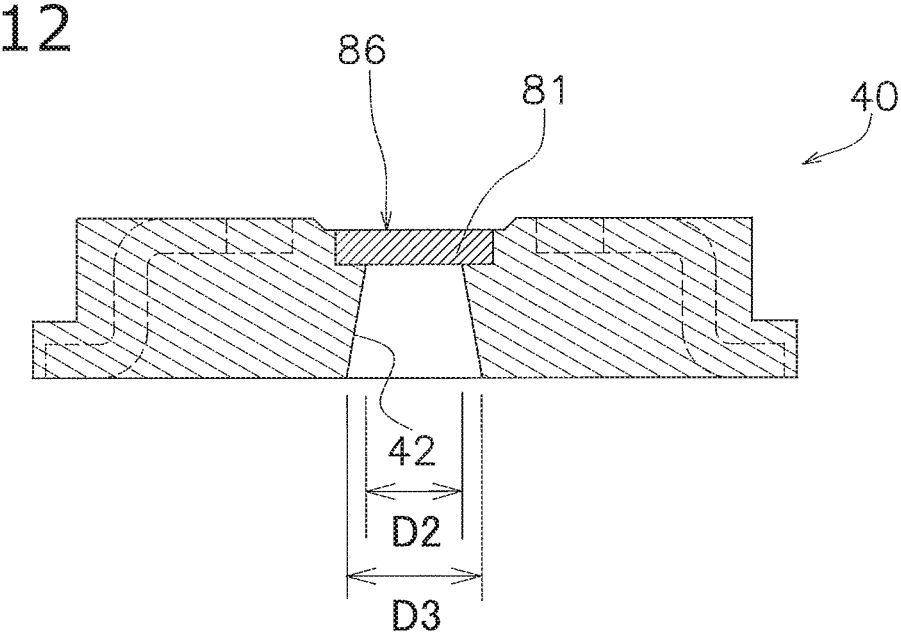
FIG. 12 is a cross-sectional view of the base taken along III-III line in FIG. 6.

FIG. 5 is a plan view of the base 40, FIG. 6 is a bottom view of the base 40, FIG. 7 is a right side view of the base 40, FIG. 8 is a front view of the base 40, and FIG. 9 is a rear view of the base 40. In addition, FIG. 10 is a cross-sectional view of the base 40 taken along I-I line in FIG. 5, FIG. 11 is a cross-sectional view of the base 40 taken along II-II line in FIG. 5, and FIG. 12 is a cross-sectional view of the base 40 taken along III-III line in FIG. 6.

The base 40 is made of thermoplastic resin by injection molding. As the thermoplastic resin used for the base 40, there is liquid crystal polymer, for example. The base 40 is a plate-like member. The front right side corner of the base 40 is chamfered to form a chamfered surface 40a. The base 40 has a vertical length L2 of e.g. 2.7 mm, a horizontal length L3 of e.g. 3.4 mm, and a height H2 of e.g. 0.7 min. A recessed portion 41 is formed from the center to the rear of the base 40. The recessed portion 41 has a rectangular shape in a plan view. A length L4 in the left/right direction of the recessed portion 41 is e.g. 0.8 mm, and a length L5 in the front/rear direction is e.g. 1.2 mm. The left/right direction length L4 and the front/rear direction length L5 of the recessed portion 41 are preferably twice or more, and more preferably five times or more than the left/right direction length and the front/rear direction length of the gas detector 61, respectively, so that gas can be easily guided into the recessed portion 41.

In the base 40, embedded are a first electrode 81, a second electrode 82, and a third electrode 83, which are made of metal. The first electrode 81, the second electrode 82, and the third electrode 83 are formed by plating nickel on stainless steel, for example. The stainless steel with nickel plated is suitable for electric welding of the first to third lead wires 62 to 64 made of platinum wire (see FIG. 3). Note that the material that is used for the first to third electrodes 81 to 83 is not limited to stainless steel with nickel plated, but metal other than stainless steel, e.g. copper, gold, iron, or an alloy thereof can be used. In addition, surface plating of the electrode is not limited to nickel plating, but other metal such as tin can be used for plating. The first to third electrodes 81 to 83 surround periphery of the recessed portion 41, the first electrode 81 is disposed in the front part of the base 40, the second electrode 82 is disposed in the right side of the base 40, and the third electrode 83 is disposed in the left side of the base 40.

As shown in FIG. 3, the second electrode 82 and the third electrode 83 are offset backward from the first electrode 81, and an offset of the second electrode 82 is different from that of the third electrode 83. The second electrode 82 is offset backward from the first electrode 81 more than the third electrode 83. In other words, the first electrode 81, the second electrode 82, and the third electrode 83 are arranged so that an offset amount L6 of a front end 82a of the second electrode 82 from a rear end 81b of the first electrode 81 (distance between the rear end 81b and the front end 82a) is larger than an offset amount L7 of a front end 83a of the third electrode 83 from the rear end 81b of the first electrode 81 (distance between the rear end 81b and the front end 83a). With this arrangement, the second electrode 82 and the third electrode 83 can be disposed at suitable positions for the second lead wire 63 and the third lead wire 64 extending from winding start and winding end of the coil-shaped heater 61b, respectively.

The first to third electrodes 81 to 83 have a width W1 of e.g. 0.7 mm. Note that the first to third electrodes 81 to 83 have the same electrode widths in this description, but this is not inevitable, and they can have different widths. However, if the first to third electrodes 81 to 83 have the same shape, the components can be commonized, and the number of components can be reduced. Each of the first to third electrodes 81 to 83 has a first crank 84 and a second crank 85 bent in opposite directions in the upper part and the lower part (see FIGS. 10 and 11). Each of the first to third electrodes 81 to 83 is embedded in resin at a portion between the first crank 84 and the second crank 85. An exposed upper part region 86 from the first crank 84 to one end 84a spreads in a two-dimensional manner, and hence the first to third lead wires 62 to 64 can be easily placed on the first to third electrodes 81 to 83, respectively. An exposed lower part region 87 from the second crank 85 to the other end 85a spreads in a two-dimensional manner, and hence an easy contact shape as a device terminal can be achieved while reducing a height H3 of the first to third electrodes 81 to 83.

The height H3 of each of the first to third electrodes 81 to 83 from the upper part to the lower part is set to be lower than a height of the package 15 by 0.3 mm or more. For example, in this description, the height H3 of the first electrode 81 from the upper part to the lower part is 0.65 mm, for example, and the height H3 of the second electrode 82 and the third electrode 83 from the upper part to the lower part is 0.7 mm, for example. Since the height H1 of the package 15 is 1.25 mm, for example, the height H3 of the second electrode 82 and the third electrode 83 from the upper part to the lower part is lower by 0.55 mm. Using the difference between the height H1 and the height H3, a space for taking gas is formed above the gas detector 61.

In a bottom part 40b of the base 40A, formed are a first opening 42, a second opening 43 and a third opening 44, which communicate to the first to third electrodes 81 to 83. Each of the first opening 42, the second opening 43, and the third opening 44 is tapered so that an opening diameter becomes smaller as being closer to the first to third electrodes 81 to 83. An opening diameter D2 of the smallest part of the first to third openings 42 to 44 is 0.4 mm, for example, and an opening diameter D3 of the largest part thereof is 0.6 mm, for example.

(2-3) Cap

Figure 13:
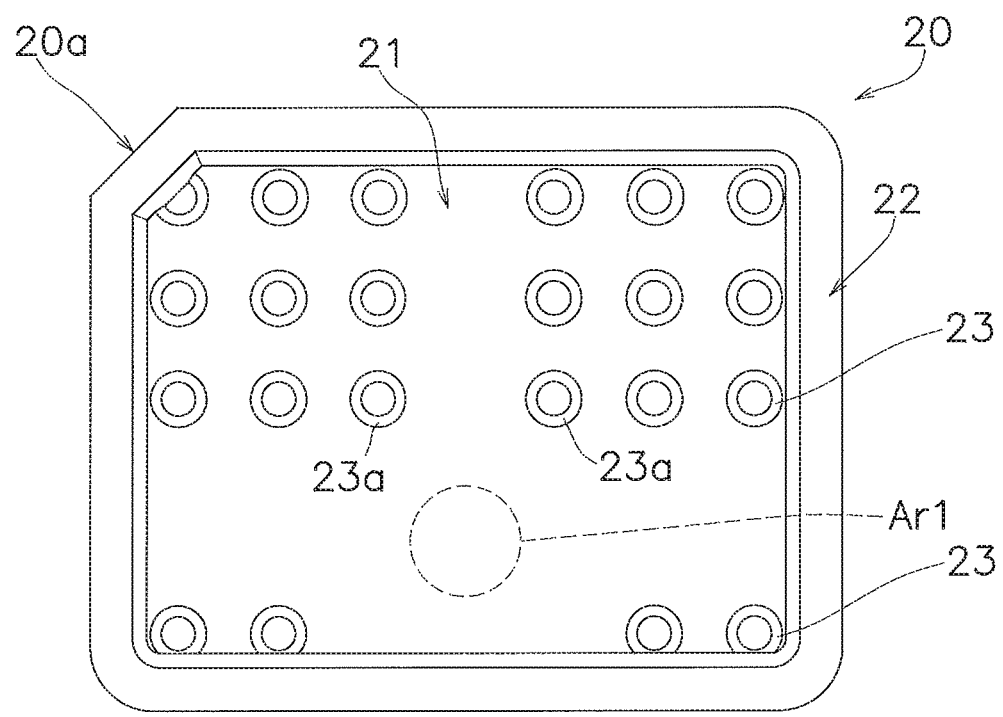
FIG. 13 is a bottom view of the cap.
Figure 14:
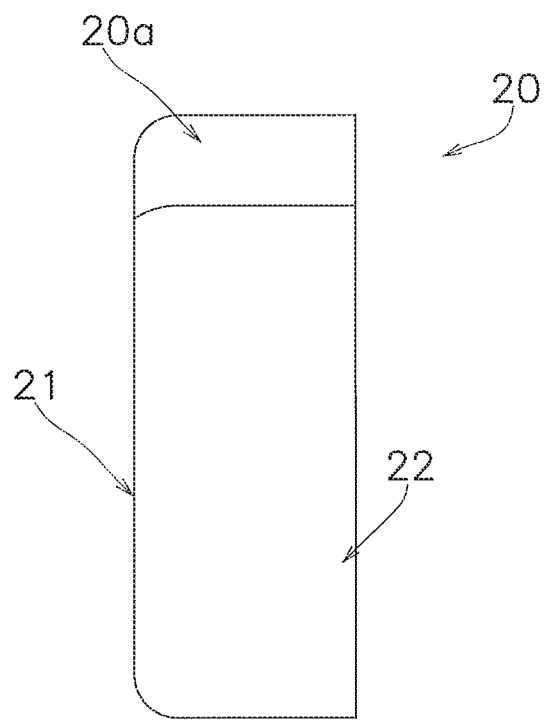
FIG. 14 is a right side view of the cap.
Figure 15:
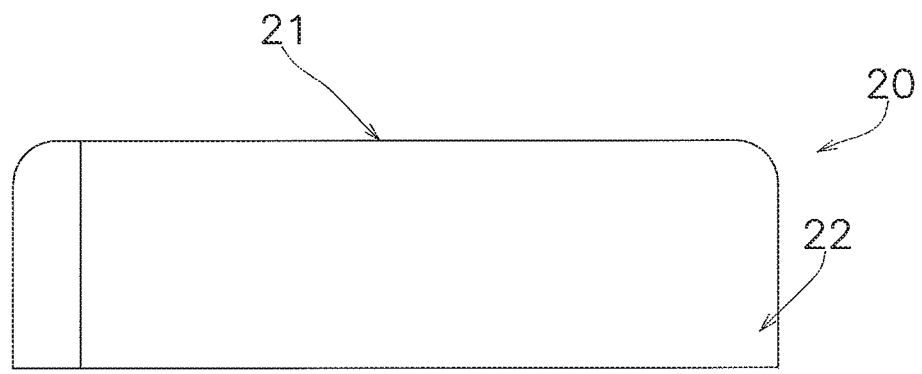
FIG. 15 is a front view of the cap.
Figure 16:
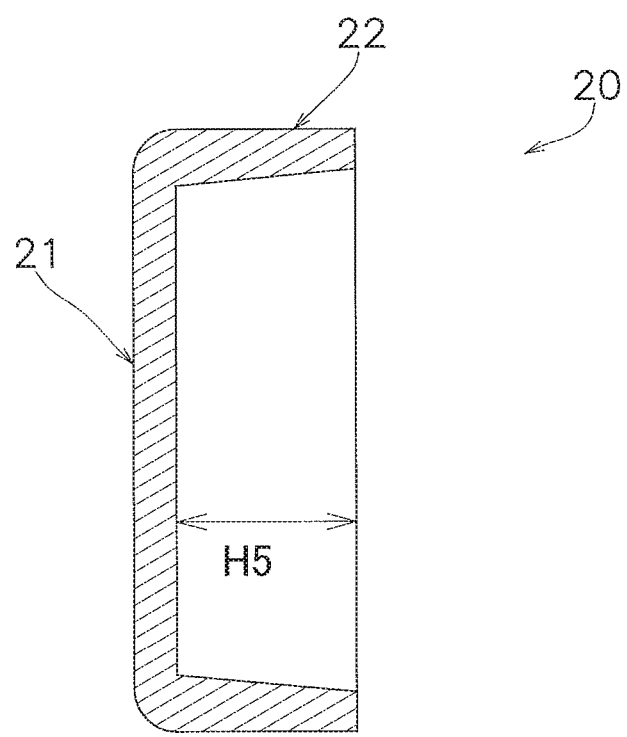
FIG. 16 is a cross-sectional view of the cap taken along IV-IV line in FIG. 2.
Figure 17:
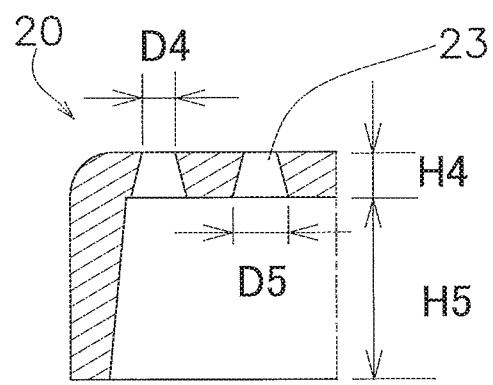
FIG. 17 is a cross-sectional view of the cap taken along V-V line in FIG. 2.

FIG. 12 is a plan view of the cap 20, FIG. 13 is a bottom view of the cap 20, FIG. 14 is a right side view of the cap 20, and FIG. 15 is a front view of the cap 20. In addition, FIG. 16 is a cross-sectional view of the cap 20 taken along IV-IV line in FIG. 2, and FIG. 17 is a cross-sectional view of the cap 20 taken along V-V line in FIG. 2.

The cap 20 includes a flat plate-like ceiling part 21, and a peripheral part 22 surrounding periphery of the ceiling part 21. A chamfered surface 20a, which corresponds to the chamfered surface 40a of the base 40, is formed on the cap 20, too. A thickness H4 of the ceiling part 21 in the height direction is 0.2 mm, for example. In addition, a height H5 of the peripheral part 22 to the bottom surface of the ceiling part 21 is 0.8 mm, for example.

Twenty-two through holes 23 are formed in the ceiling part 21. These through holes 23 are arranged in a region other than a detector disposed region Ar1 just above a region in which the gas detector 61 is disposed. Two through holes 23a among them are positioned just above the recessed portion 41 of the base 40. The through hole 23 is tapered so that a through hole diameter is increased toward the base 40. A through hole diameter D4 of the smallest part of the through hole 23 is 0.15 mm, for example, and a through hole diameter D5 of the largest part thereof is 0.25 mm, for example. Since the through hole 23 increases its diameter toward inside of the package 15 in this way, dust or water drops hardly enter while gas can be easily guided to the inside.

(2-4) Package

Figure 18:
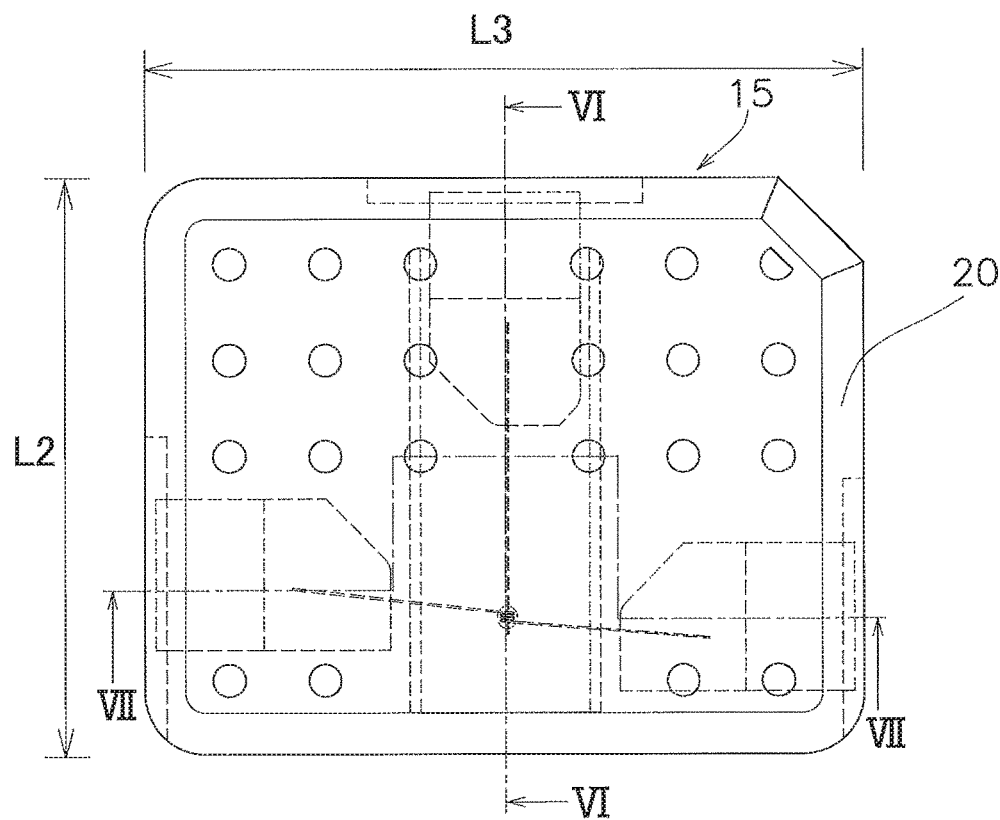
FIG. 18 is a plan view of a package.
Figure 19:
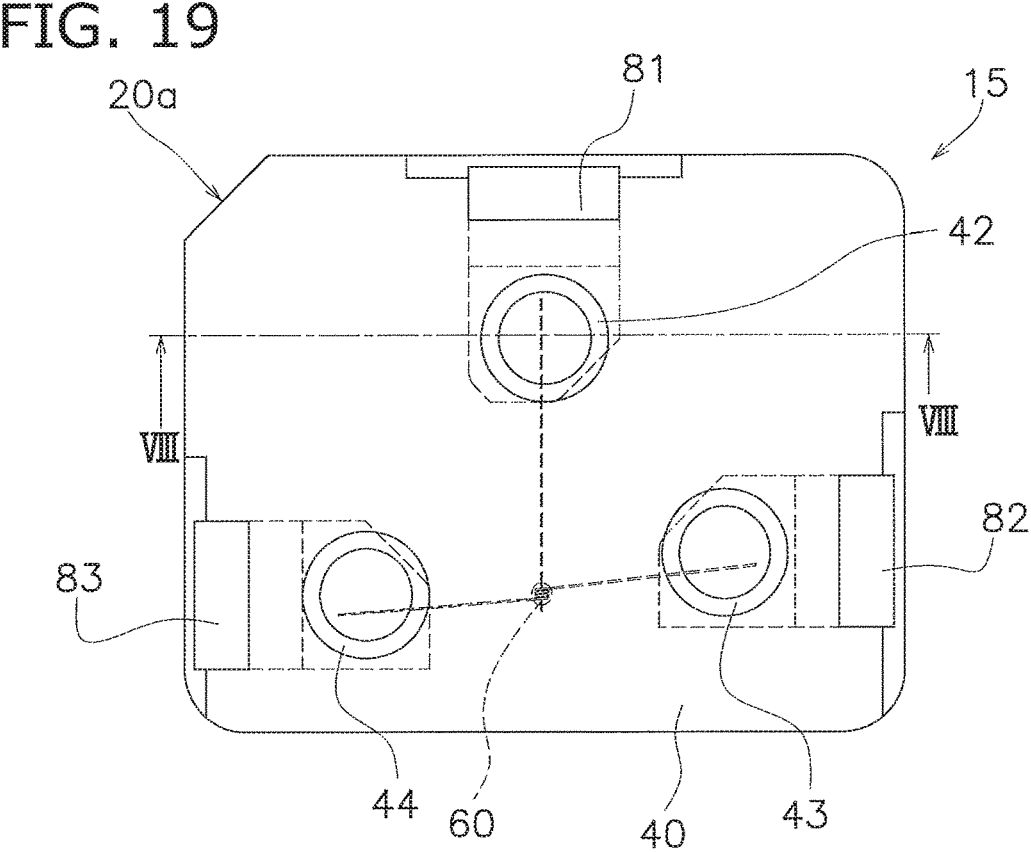
FIG. 19 is a bottom view of the package.
Figure 20:
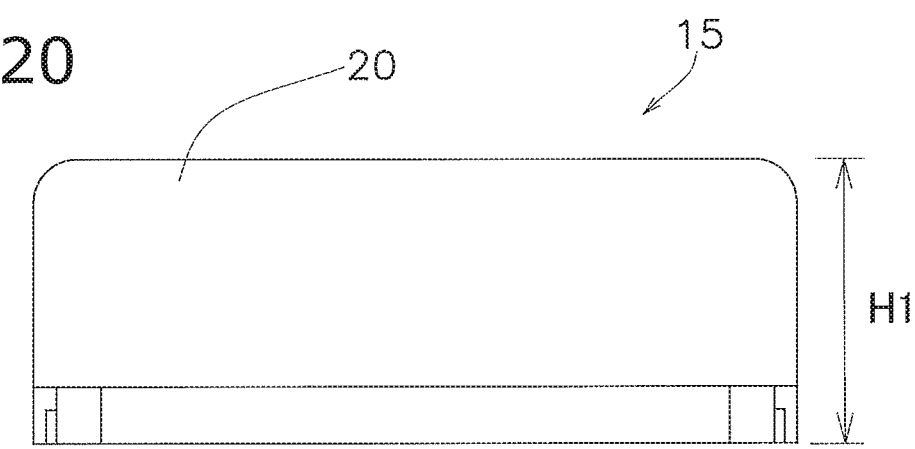
FIG. 20 is a rear view of the package.
Figure 21:
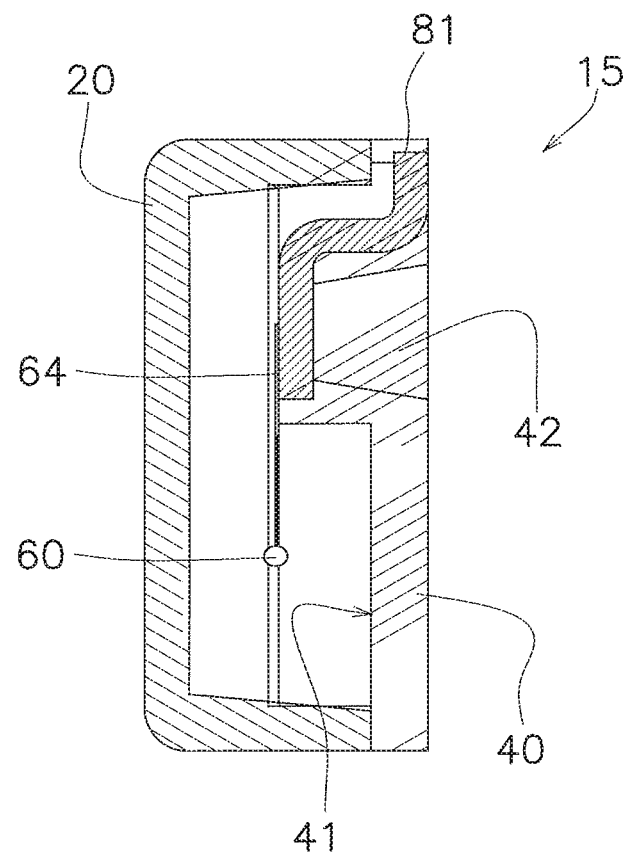
FIG. 21 is a cross-sectional view of the package taken along VI-VI line in FIG. 18.
Figure 22:
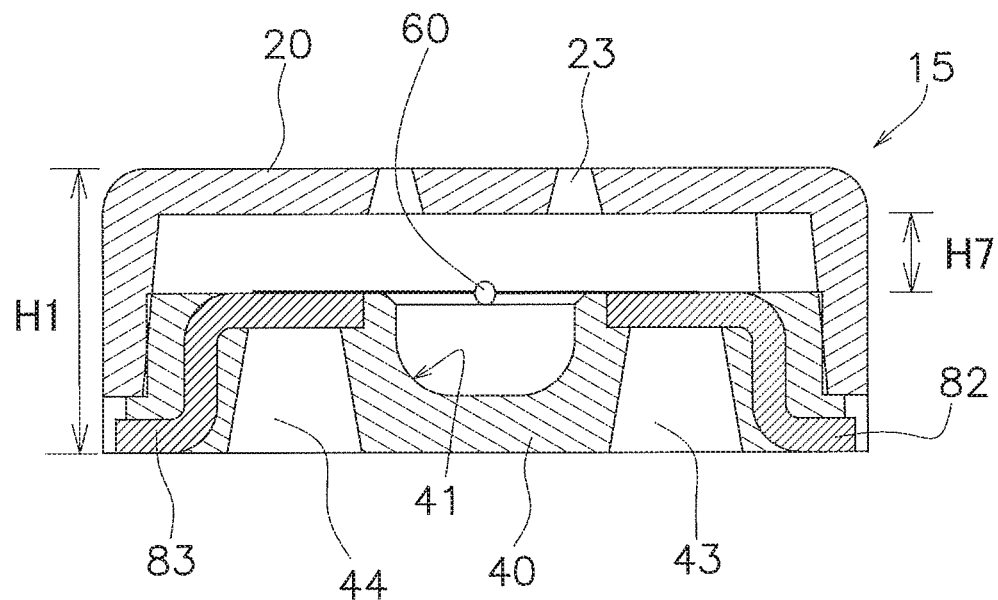
FIG. 22 is a cross-sectional view of the package taken along VII-VII line in FIG. 18.
Figure 23:
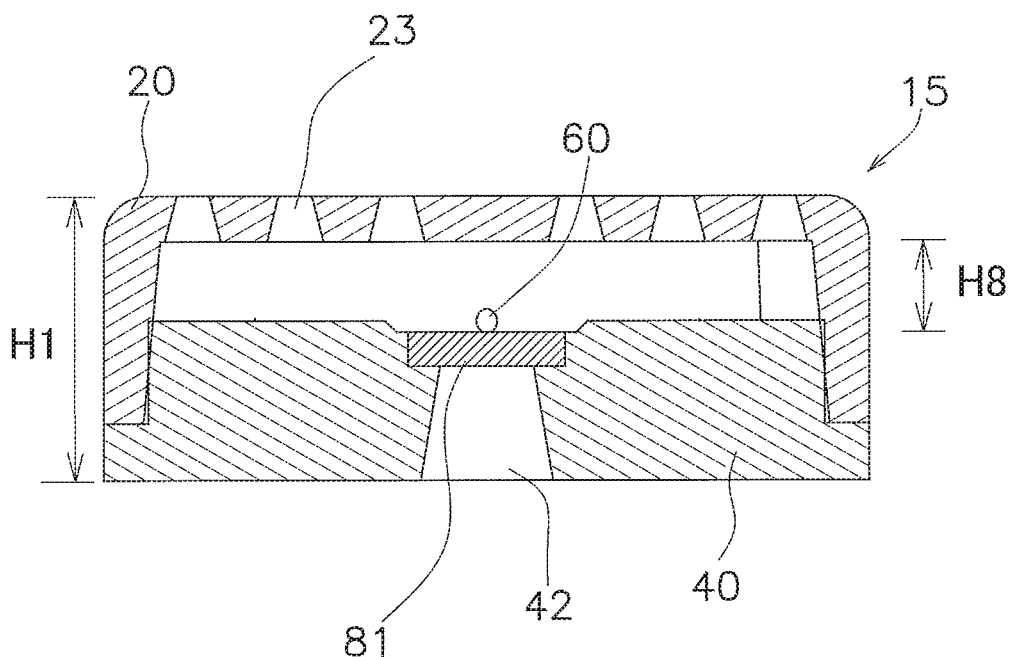
FIG. 23 is a cross-sectional view of the package taken along VIII-VIII line in FIG. 19.

FIG. 18 is a plan view of the package 15, FIG. 19 is a bottom view of the package 15, and FIG. 20 is a rear view of the package 15. In addition, FIG. 21 is a cross-sectional view of the package 15 taken along VI-VI line in FIG. 18, FIG. 22 is a cross-sectional view of the package 15 taken along VII-VII line in FIG. 18, and FIG. 23 is a cross-sectional view of the package 15 taken along VIII-VIII line in FIG. 19.

The height H1 of the package 15 is 1.25 mm, for example. A height H7 of the space in the package 15 between the cap 20 and the base 40 is 0.35 mm, for example. However, a height H8 from the first electrode 81 to a lower surface of the ceiling part 21 of the cap 20 is 0.4 mm, for example. As described above, the vertical length L2 of the package 15 is the same as the vertical length of the base 40, and the horizontal length L3 of the package 15 is the same as the horizontal length of the base 40.

(3) Method of Manufacturing Gas Sensor Device

For manufacturing of the gas sensor device 10, the cap 20, the base 40, and the gas detecting element 60 are prepared. In this description, a case where the cap 20, the base 40, and the gas detecting element 60 are prepared independently in parallel is exemplified and described. The cap 20 is molded from thermoplastic resin by injection molding method using a die. The base 40 is molded from thermoplastic resin by insert molding method using a die, in a state where the first electrode 81, the second electrode 82, and the third electrode 83 are embedded. The base 40 is formed by the process shown in FIGS. 24 to 27, for example.

Figure 24:
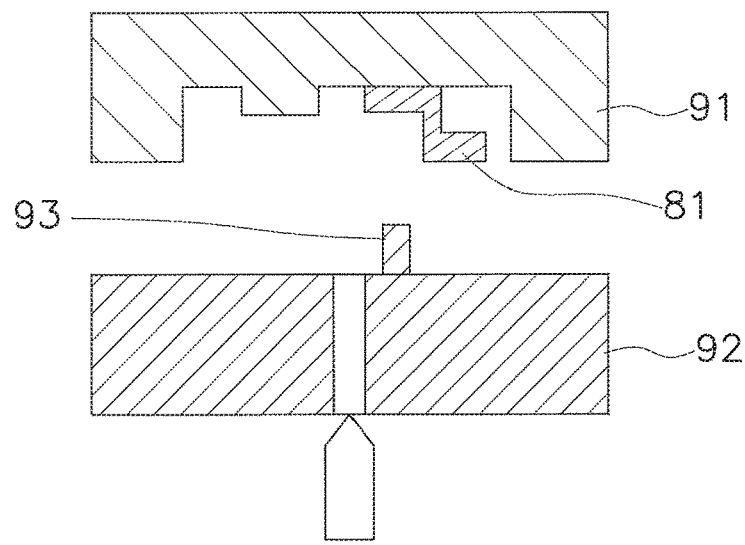
FIG. 24 is a schematic cross-sectional view showing a mold opening step in injection molding of the base.

First, as shown in FIG. 24, the first electrode 81 is set in a first mold 91 in a state where the first mold 91 and a second mold 92 are opened. Although the second electrode 82 and the third electrode 83 are omitted in FIG. 24, these are also set in the first mold 91 in the same manner as the first electrode 81. A fixing pin 93 has been attached to the second mold 92. Although not shown in FIG. 24, other two fixing pins for fixing the second electrode 82 and the third electrode 83 have been also attached to the second mold 92. In order to hold the first to third electrodes 81 to 83 in the set state without moving, small through holes are formed in the first mold 91, and the first to third electrodes 81 to 83 are sucked and attracted, for example.

Figure 25:
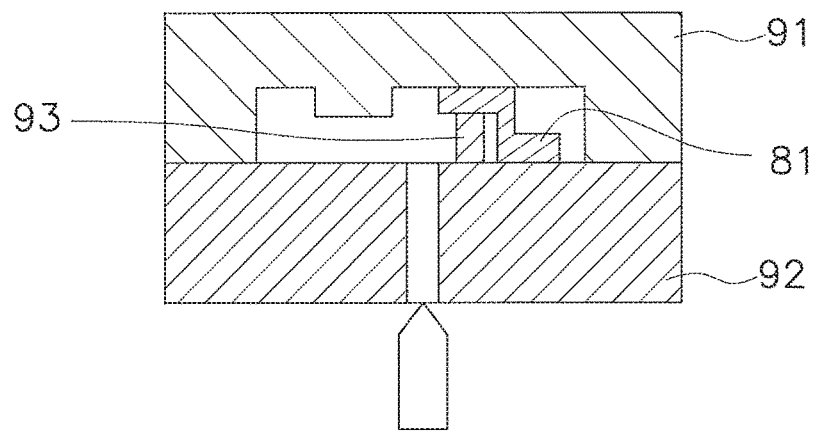
FIG. 25 is a schematic cross-sectional view showing a state in which the mold is closed in the injection molding of the base.

Next, as shown in FIG. 25, the first mold 91 and the second mold 92 are clamped. In the state where the first mold 91 and the second mold 92 are clamped, the fixing pin 93 abuts the first electrode 81, and the first electrode 81 is fixed by the fixing pin 93 so as not to move. The second electrode 82 and the third electrode 83 are also fixed by other two fixing pins that are not shown.

Figure 26:
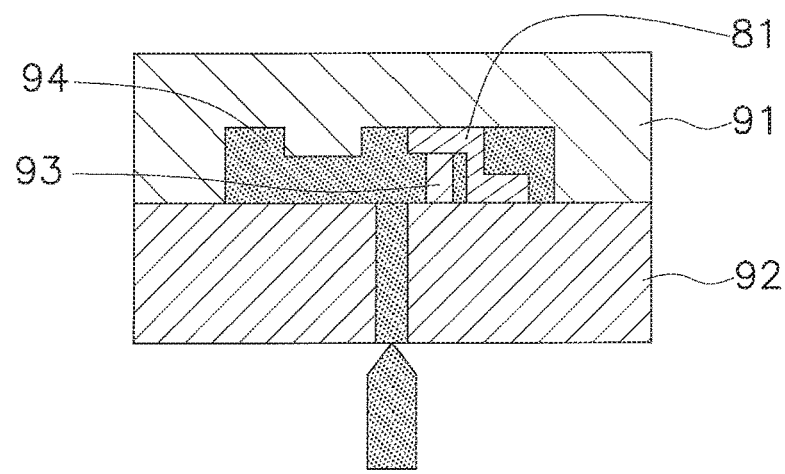
FIG. 26 is a schematic cross-sectional view showing an injection molding step of the base.

Next, as shown in FIG. 26, melted thermoplastic resin 94 is injected into a cavity surrounded by the first mold 91 and the second mold 92.

Figure 27:
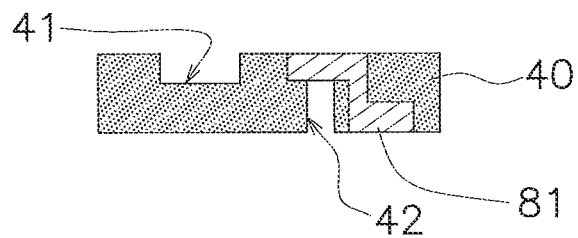
FIG. 27 is a schematic cross-sectional view for describing the base made by injection molding.

FIG. 27 shows the base 40 taken out after opening the first mold 91 and the second mold 92 after injection molding. A part in which the fixing pin 93 existed becomes the first opening 42, and parts in which other not shown fixing pins existed become the second opening 43 and the third opening 44 (see FIG. 11).

Figure 28:
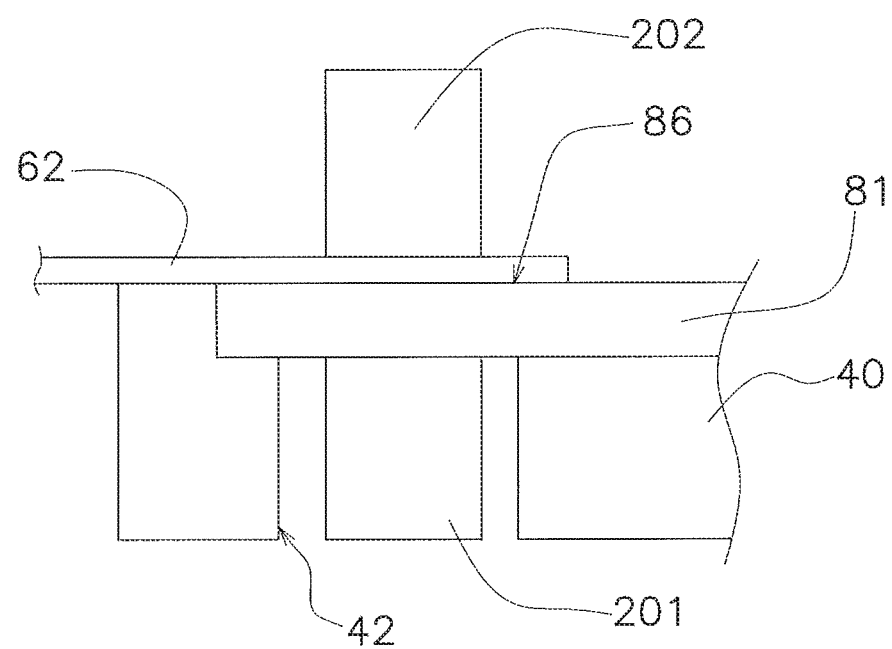
FIG. 28 is a schematic cross-sectional view for describing electric welding.

FIG. 28 shows a method of electric welding of the gas detecting element 60. The first lead wire 62 is placed on the upper part region 86 of the first electrode 81. A first power supply line 201 of a welding machine is pressed to the first electrode 81 from below the base 40 through the first opening 42. A second power supply line 202 of the welding machine is pressed to the first lead wire 62 from above the base 40. In the state shown in FIG. 28, if a current flows from the first power supply line 201 to the second power supply line 202 through the first electrode 81 and the first lead wire 62, and then the heat is generated between the first electrode 81 and the first lead wire 62, so that the first electrode 81 and the first lead wire 62 are incited and welded.

By repeating the same electric welding also between the second electrode 82 and the second lead wire 63 as well as between the third electrode 83 and the third lead wire 64, as shown in FIG. 3, the gas detecting element 60 is mounted on the base 40.

The above example describes the case where the first to third lead wires 62 to 64 of the gas detecting element 60 in which the gas sensing body 61a has been formed are electrically welded to the first electrode 81 to the third electrode 83, but it is possible to first perform electric welding of the first to third lead wires 62 to 64 to the first to third electrodes 81 to 83, and then to form the gas sensing body 61a in the first to third lead wires 62 to 64 and the heater 61b.

(4) Gas Detecting Apparatus Using Gas Sensor Device

Figure 29:
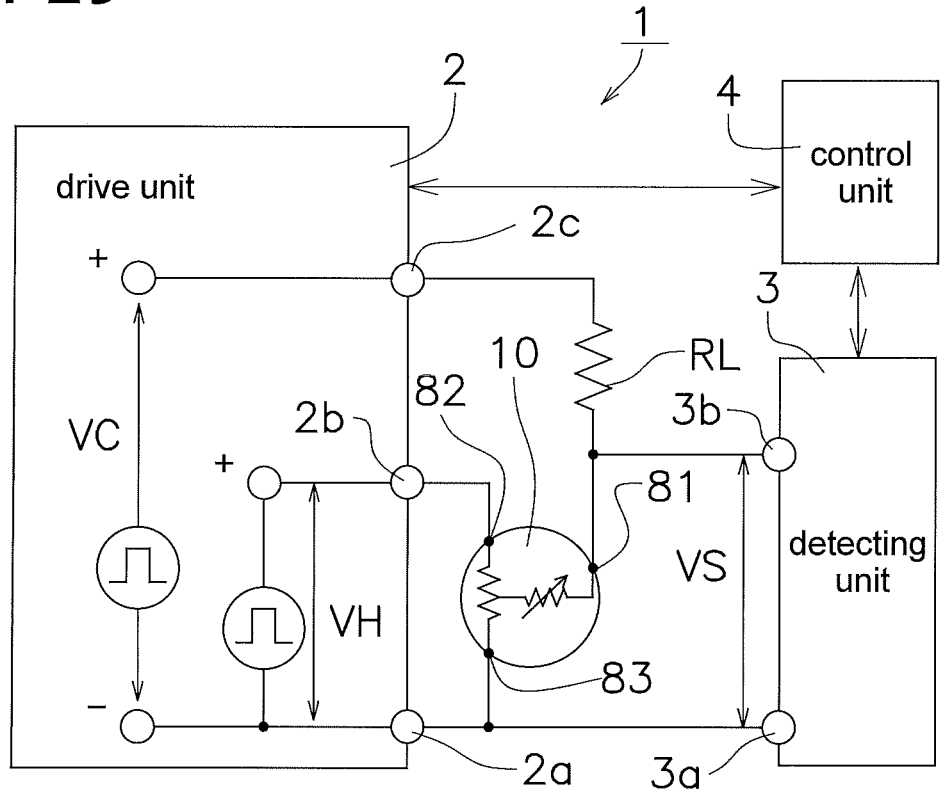
FIG. 29 is a circuit diagram of a gas detecting apparatus using the gas sensor device.

A gas detecting apparatus 1 configured by using the gas sensor device 10 described above includes, as shown in FIG. 29, the gas sensor device 10, a drive unit 2 that outputs a drive voltage to the gas sensor device 10, a detector 3 that detects a voltage at a predetermined point in the gas sensor device 10, a control unit 4 connected to the drive unit 2 and the detector 3 so as to control the gas detecting apparatus 1, and a load resistor RL. In this description, the detector 3 detects a voltage VS generated between the first electrode 81 and the second and third electrodes 82 and 83, which are also heater electrodes. Then, the control unit 4 detects target gas based on a resistance value between the third electrode 83 and the first electrode 81.

In the gas sensor device 10, a voltage is applied to the heater 61b for a very short time of e.g. 0.1 seconds or less for heating the heater 61b. In other words, the gas detecting apparatus 1 heats the heater 61b by applying the voltage to the heater 61b only for a predetermined period before measurement, and in other period no voltage is applied to the heater 61b for measurement. In this way, an increase in temperature of the gas sensor device 10, in particular an increase in ambient temperature of the gas detecting element 60 is prevented. In this description, the voltage applied to the heater 61b is a rectangular wave so that much heat can be generated in a short time, but without limiting to the rectangular wave, the applied voltage can be a sine wave, for example.

Figure 30A:
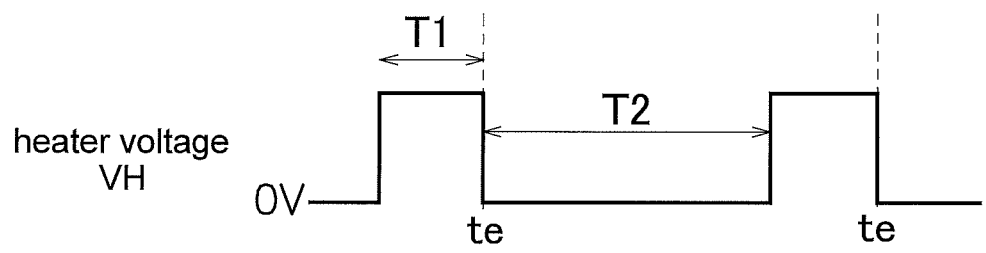
FIG. 30A is a waveform diagram of a heater voltage.

The drive unit 2 has a GND terminal 2a connected to a GND terminal 3a of the detector 3 and the third electrode 83 of the gas sensor device 10. The drive unit 2 has a heater terminal 2b connected to the second electrode 82 of the gas sensor device 10. A heater voltage VH applied between the GND terminal 2a and the heater terminal 2b of the drive unit 2 is a pulse voltage as shown in FIG. 30A. In this description, for one-time gas detection, the heater 61b of the gas sensor device 10 is heated by the one pulse shown in FIG. 30A, for example. An application period T1 of this one pulse is 0.06 sec, for example. Power consumed by the heater 61b during this one pulse is approximately 100 mW, for example. In order to prevent overheating of the gas sensor device 10, an interval T2 between pulses is a few seconds or more, for example, which is set corresponding to an interval of gas detection. Note that one result of gas detection can be a result of one set of plurality of times of gas detection using a plurality of pulse voltages.

The first electrode 81 of the gas sensor device 10 is connected to a detection terminal 3b of the detector 3. This detector 3 detects the voltage VS generated between the first electrode 81 and the third electrode 83. The control unit 4 measures a resistance value between the first electrode 81 and the third electrode 83 from the voltage VS detected by the detector 3, thereby detecting the target gas.

Figure 30B:
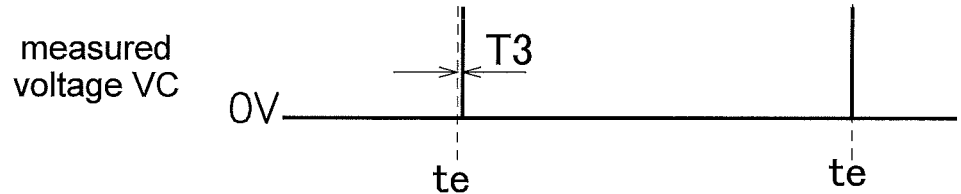
FIG. 30B is a waveform diagram of a measured voltage.

The drive unit 2 applies a measured voltage VC to the first electrode 81 via the load resistor RL in order to generate the voltage VS measured by the detector 3. Therefore, a measured voltage terminal 2c of the drive unit 2 is connected to one end of the load resistor RL, and the other end of the load resistor RL is connected to the first electrode 81 and the detection terminal 3b. A resistance value of the load resistor RL is 10 kΩ, for example, and the measured voltage VC is set within the range of one to a few volts, for example. As shown in FIG. 30B, the measured voltage VC is applied in +/−0.1 msec from time point te when application of the heater voltage VH is finished.

In the gas detecting apparatus 1, heat capacity of the gas detecting element 60, in particular heat capacity of the gas detector 61 is small, and hence power consumption of the heater 61b becomes small. In addition, because the gas detecting apparatus 1 has small heat capacity, it has good thermal response characteristics so that a target gas can be detected in a short time.

(5) Characteristics (5-1)

In the gas sensor device 10 described above, the first to third metal lead wires 62 to 64 are connected to the three metal electrodes, i.e. the first to third electrodes 81 to 83 disposed around the recessed portion 41 of the base 40, and hence the gas detector 61 including the heater 61b is held in a suspended state in the recessed portion 41 and the space above the recessed portion 41. Therefore, as the gas detector 61 is made smaller, the recessed portion 41 is made smaller, and the first to third electrodes 81 to 83, which are accurately disposed to surround the recessed portion 41, can also made smaller and disposed more densely. As a result, an occupied area of the recessed portion 41 and the first to third electrodes 81 to 83 around the recessed portion 41 can be reduced, and hence the entire shape of the gas sensor device 10 can be downsized.

(5-2)

In the cap 20, the plurality of the through holes 23 are formed in a region other than the region just above the gas detector 61, and hence a part of the cap 20 corresponding to the detector disposed region Ar1 shuts off dust and water drops, so that dust can hardly adhere to the gas detector 61.

(5-3)

Each of the three wires, i.e. the first to third electrodes 81 to 83 has the first crank 84 and the second crank 85, which are bent in opposite directions in the upper part and the lower part, a part between the first crank 84 and the second crank 85 that is embedded in the base 40, and a side closer to the one end 84a than the first crank 84 that is exposed upward from the base 40, and a part closer to the other end 85a than the second crank 85 that is exposed downward from the base 40. Because the exposed upper part region 86 from the first crank 84 to the one end 84a spreads in a two-dimensional manner, the first to third lead wires 62 to 64 can be easily placed. In addition, because the exposed lower part region 87 from the second crank 85 to the other end 85a spreads in a two-dimensional manner, easy contact shape as a device terminal can be achieved. Because the part between the first crank 84 and the second crank 85 is embedded, the first to third electrodes 81 to 83 are securely fixed to the base 40 so that the gas detecting element 60 can also be securely fixed to the package 15.

(5-4)

The two wires, i.e. the second lead wire 63 and the third lead wire 64 forms the heater 61b, in which a part of the lead wire, i.e. the connection portion between the second lead wire 63 and the third lead wire 64 is wound in a three turn coil in the gas detecting element 60. Because the number of turns of the coiled heater 61b is three, the heater 61b can be downsized, and hence the gas detecting element 60 can be small, so that downsizing of the gas sensor device 10 can be achieved.

(5-5)

As described above with reference to FIGS. 3 and 4, the second lead wire 63 and the third lead wire 64, which extend directly from the coiled heater 61b, are offset from each other due to the shape of the heater 61b. However, because the second electrode and the third electrode are disposed at appropriate positions for the second lead wire 63 and the third lead wire 64 according to the offset between the second lead wire 63 and the third lead wire 64, the gas sensor device 10 can be easily downsized.

(5-6)

In the method of manufacturing the gas sensor device 10, as described above with reference to FIG. 28, the first lead wire 62 is electrically welded to the first electrode 81 while the first lead wire 62, which extends from the gas detector 61 including the heater 61b, and the first electrode 81 are respectively contacted with the first power supply line 201 and the second power supply line 202 of the welding machine from above and below the base 40. This electric welding is performed in the state where the first lead wire 62 is placed on the first electrode 81 embedded in the base 40, and the gas detector 61 is suspended in the recessed portion 41 and the space above the recessed portion 41 so that the gas detector 61 does not contact with walls of the recessed portion 41. Further, the welding position is within the vertical and horizontal range of the base 40. This electric welding is also performed between the second lead wire 63 and the second electrode 82 as well as between the third lead wire 64 and the third electrode 83 in the same manner. As a result, the first to third electrodes 81 to 83 can be within a vertical range of 2.7 mm and a horizontal range of 3.4 mm. In addition, because the two power supply lines, i.e. the first power supply line 201 and the second power supply line 202 of the welding machine are made contact from above and below, they can contact more easily than a case where the both power supply lines are made contact from above, and hence the very compact package 15 can be easily manufactured. Note that the gas detector 61 is suspended in the recessed portion 41 and the space above the recessed portion 41 in the embodiment described above, but the gas detector 61 can be suspended in a space within the recessed portion 41, or the gas detector 61 can be suspended in the space above the recessed portion 41.

(5-7)

In the method of manufacturing the gas sensor device 10, in the step of forming the base 40, the first to third openings 42 to 44, communicating the bottom part and the three electrodes, i.e. the first to third electrodes 81 to 83, are formed by the fixing pins 93 for holding the first to third electrodes 81 to 83. Because the first to third openings 42 to 44 are formed by the fixing pins 93 simultaneously when the base 40 is formed, the first to third openings 42 to 44 can be formed without increasing the number of manufacturing steps. Further, by inserting the first power supply line 201 in each of the first to third openings 42 to 44, it can be easily positioned contacting with each of the first to third electrodes 81 to 83, and hence electric welding can be performed fast and easily for the very small gas sensor device 10, so that manufacturing time can be reduced.

(6) Variations (6-1) Variation 1A

The above embodiment describes the case where the coil-shaped heater 61b is disposed in the gas sensing body 61a, but the present disclosure can be applied to a case where a catalyst such as a platinum wire is wound in a coil, and the coil-shaped heater is exposed in use, like a contact combustion type gas sensor.

While only selected embodiments have been chosen to illustrate the present disclosure, it will be apparent to those skilled in the art from this disclosure that various changes and modifications can be made herein without departing from the scope of the advancement as defined in the appended claims. Furthermore, the foregoing descriptions of the embodiments according to the present disclosure are provided as examples only, and not for the purpose of limiting the advancement as defined by the appended claims and their equivalents. Thus, the scope of the disclosure is not limited to the disclosed embodiments.

What is claimed is:

1. A gas sensor device comprising:
a package including a cap in which at least one tapered through hole for taking gas is formed and a base in which a recessed portion is formed, a height of the package being 5 mm or less from an uppermost portion of the cap to a lowermost portion of the base, in a state where the cap is attached to the base so that a space is defined around the recessed portion;
a plurality of metal electrodes fixed to portions surrounding the recessed portion and embedded in the base; and
a gas detecting element, which includes a gas detector having a coil-shaped heater that is heated when detecting a predetermined gas, and a plurality of metal lead wires extending from the gas detector to the plurality of electrodes, wherein the gas detecting element is held in a suspended state in the recessed portion and/or a space above the recessed portion with the plurality of lead wires, so that the gas detecting element, which includes the heater, does not make contact with walls of the recessed portion.

2. The gas sensor device according to claim 1, wherein the cap has a plurality of tapered through holes formed in parts other than a part just above the gas detector.

3. The gas sensor device according to claim 2, wherein each of the plurality of electrodes has a first crank and a second crank bent in opposite directions in an upper part and in a lower part, and a part between the first crank and the second crank that is embedded in the base, and each of the electrodes further includes a side closer to one end than the first crank that is exposed upward from the base, and a side closer to the other end than the second crank that is exposed downward from the base.

4. The gas sensor device according to claim 3, wherein at least one of the plurality of lead wires forms the heater in which a part of lead wire is coiled in five or less turns in the gas detecting element.

5. The gas sensor device according to claim 4, wherein the plurality of lead wires includes a first lead wire extending from the gas detector, and second and third lead wires extending directly from the coil-shaped heater, the plurality of electrodes includes a first electrode, a second electrode, and a third electrode, the second lead wire is welded to the second electrode, the third lead wire is welded to the third electrode, the first electrode is disposed at a frontmost position, and a distance from a rear end of the first electrode to a front end of the second electrode is longer than a distance from the rear end of the first electrode to a front end of the third electrode.

6. The gas sensor device according to claim 1, wherein each of the plurality of electrodes has a first crank and a second crank bent in opposite directions in an upper part and in a lower part, and a part between the first crank and the second crank that is embedded in the base, and each of the electrodes further includes a side closer to one end than the first crank that is exposed upward from the base, and a side closer to the other end than the second crank that is exposed downward from the base.

7. The gas sensor device according to claim 6, wherein at least one of the plurality of lead wires forms the heater in which a part of lead wire is coiled in five or less turns in the gas detecting element.

8. The gas sensor device according to claim 7, wherein the plurality of lead wires includes a first lead wire extending from the gas detector, and second and third lead wires extending directly from the coil-shaped heater, the plurality of electrodes includes a first electrode, a second electrode, and a third electrode, the second lead wire is welded to the second electrode, the third lead wire is welded to the third electrode, the first electrode is disposed at a frontmost position, and a distance from a rear end of the first electrode to a front end of the second electrode is longer than a distance from the rear end of the first electrode to a front end of the third electrode.

9. The gas sensor device according to claim 6, wherein the plurality of lead wires includes a first lead wire extending from the gas detector, and second and third lead wires extending directly from the coil-shaped heater, the plurality of electrodes includes a first electrode, a second electrode, and a third electrode, the second lead wire is welded to the second electrode, the third lead wire is welded to the third electrode, the first electrode is disposed at a frontmost position, and a distance from a rear end of the first electrode to a front end of the second electrode is longer than a distance from the rear end of the first electrode to a front end of the third electrode.

10. The gas sensor device according to claim 1, wherein at least one of the plurality of lead wires forms the heater in which a part of lead wire is coiled in five or less turns in the gas detecting element.

11. The gas sensor device according to claim 10, wherein the plurality of lead wires includes a first lead wire extending from the gas detector, and second and third lead wires extending directly from the coil-shaped heater, the plurality of electrodes includes a first electrode, a second electrode, and a third electrode, the second lead wire is welded to the second electrode, the third lead wire is welded to the third electrode, the first electrode is disposed at a frontmost position, and a distance from a rear end of the first electrode to a front end of the second electrode is longer than a distance from the rear end of the first electrode to a front end of the third electrode.

12. The gas sensor device according to claim 2, wherein at least one of the plurality of lead wires forms the heater in which a part of lead wire is coiled in five or less turns in the gas detecting element.

13. The gas sensor device according to claim 12, wherein the plurality of lead wires includes a first lead wire extending from the gas detector, and second and third lead wires extending directly from the coil-shaped heater, the plurality of electrodes includes a first electrode, a second electrode, and a third electrode, the second lead wire is welded to the second electrode, the third lead wire is welded to the third electrode, the first electrode is disposed at a frontmost position, and a distance from a rear end of the first electrode to a front end of the second electrode is longer than a distance from the rear end of the first electrode to a front end of the third electrode.

14. The gas sensor device according to claim 2, wherein the plurality of lead wires includes a first lead wire extending from the gas detector, and second and third lead wires extending directly from the coil-shaped heater, the plurality of electrodes includes a first electrode, a second electrode, and a third electrode, the second lead wire is welded to the second electrode, the third lead wire is welded to the third electrode, the first electrode is disposed at a frontmost position, and a distance from a rear end of the first electrode to a front end of the second electrode is longer than a distance from the rear end of the first electrode to a front end of the third electrode.

15. The gas sensor device according to claim 3, wherein the plurality of lead wires includes a first lead wire extending from the gas detector, and second and third lead wires extending directly from the coil-shaped heater, the plurality of electrodes includes a first electrode, a second electrode, and a third electrode, the second lead wire is welded to the second electrode, the third lead wire is welded to the third electrode,
the first electrode is disposed at a frontmost position, and
a distance from a rear end of the first electrode to a front end of the second electrode is longer than a distance from the rear end of the first electrode to a front end of the third electrode.

16. The gas sensor device according to claim 1, wherein
the plurality of lead wires includes a first lead wire extending from the gas detector, and second and third lead wires extending directly from the coil-shaped heater,
the plurality of electrodes includes a first electrode, a second electrode, and a third electrode,
the second lead wire is welded to the second electrode,
the third lead wire is welded to the third electrode,
the first electrode is disposed at a frontmost position, and
a distance from a rear end of the first electrode to a front end of the second electrode is longer than a distance from the rear end of the first electrode to a front end of the third electrode.

17. A method of manufacturing the gas sensor device according to claim 1, comprising:
preparing the cap in which the at least one tapered through hole for taking gas is formed;
forming the base in which the plurality of metal electrodes are embedded, the base having the recessed portion surrounded by the plurality of electrodes and the height of 5 mm or less;
electrically welding the lead wires to the electrodes by placing the plurality of metal lead wires, which extend from the gas detector including the coil-shaped heater, on the plurality of electrodes, and by bringing power supply lines of a welding machine to contact with the lead wires and the electrodes from above and below of the base in vertical and horizontal ranges of the base, so that the gas detector is suspended in the recessed portion and/or the space above the recessed portion, without contacting with the walls of the recessed portion; and
attaching the cap to the base so as to assemble the package having a length, a width, and the height of 5 mm or less each.

18. The method of manufacturing according to claim 17, wherein
in the base forming step, openings, which communicates a bottom part and the plurality of electrodes, are formed by fixing pins for holding the electrodes, and
in the electrically welding step, a power supply line is brought to contact with an electrode through an opening.

19. A gas sensor device comprising:
a package including a cap in which a through hole for taking gas is formed and a base in which a recessed portion is formed, a height of the package being 5 mm or less from an uppermost portion of the cap to a lowermost portion of the base, in a state where the cap is attached to the base so that a space is defined around the recessed portion;
a plurality of metal electrodes fixed to portions surrounding the recessed portion and embedded in the base, the plurality of metal electrodes consisting of a first electrode disposed on a front edge of the base, a second electrode disposed on a right edge of the base, and a third electrode disposed on a left edge of the base; and
a gas detecting element, which includes a gas detector having a coil-shaped heater that is heated when detecting a predetermined gas, and a plurality of metal lead wires extending from the gas detector to the plurality of electrodes, wherein
the gas detecting element is held in a suspended state in the recessed portion and/or a space above the recessed portion with the plurality of lead wires, so that the gas detecting element, which includes the heater, does not make contact with walls of the recessed portion.

20. The gas sensor device according to claim 1, wherein the cap includes a chamfered surface corresponding to a chamfered surface of the base.

* * * * *